United States Patent
Yoshida (10) Patent No.: US 11,385,194 B2
(45) Date of Patent: Jul. 12, 2022

(54) FLUID PROPERTY DETECTION DEVICE

(71) Applicant: KYB Corporation, Tokyo (JP)

(72) Inventor: Keitaro Yoshida, Kanagawa (JP)

(73) Assignee: KYB Corporation, Tokyo (JP)

( * ) Notice: Subject to any disclaimer, the term of this patent is extended or adjusted under 35 U.S.C. 154(b) by 406 days.

(21) Appl. No.: 16/493,761

(22) PCT Filed: Mar. 1, 2018

(86) PCT No.: PCT/JP2018/007800
§ 371 (c)(1),
(2) Date: Sep. 13, 2019

(87) PCT Pub. No.: WO2018/168498
PCT Pub. Date: Sep. 20, 2018

(65) Prior Publication Data
US 2020/0033281 A1    Jan. 30, 2020

(30) Foreign Application Priority Data

Mar. 15, 2017  (JP) .............................. JP2017-049789

(51) Int. Cl.
*G01N 27/06* (2006.01)
*G01N 33/28* (2006.01)
*G01R 27/22* (2006.01)

(52) U.S. Cl.
CPC ......... *G01N 27/06* (2013.01); *G01N 33/2888* (2013.01); *G01R 27/22* (2013.01)

(58) Field of Classification Search
CPC ........ G01N 27/06; G01N 27/07; G01N 27/08; G01R 27/22
See application file for complete search history.

(56) References Cited

U.S. PATENT DOCUMENTS 4,626,413 A   12/1986  Blades et al.
4,666,860 A    5/1987  Blades et al.
(Continued)

FOREIGN PATENT DOCUMENTS

CN        101074940 A   11/2007
JP        S60-159642 A   8/1985
(Continued)

OTHER PUBLICATIONS

Brian M. Marx et al, Micro-Sensor for Monitoring Oils, 2006, IEEE (Year: 2006).*

(Continued)

*Primary Examiner* — Son T Le
*Assistant Examiner* — Dustin R Dickinson
(74) *Attorney, Agent, or Firm* — Hauptman Ham, LLP (57) ABSTRACT

A fluid property detecting device includes a detection portion configured to detect electric characteristics of a detection target fluid, a calculation portion configured to calculate a property value of the detection target fluid, and a storage portion configured to store the property value calculated by the calculation portion. The storage portion stores, in advance, as the reference detection value, the detection value of the electric characteristic of a reference fluid detected by the detection portion, and the calculation portion calculates the property value of the detection target fluid on the basis of a value obtained by subtracting the reference detection value from a detection value of the detection target fluid.

5 Claims, 4 Drawing Sheets

(56) References Cited

U.S. PATENT DOCUMENTS

| | | | |
|---|---|---|---|
| 4,868,127 | A | 9/1989 | Blades et al. |
| 5,047,212 | A | 9/1991 | Blades et al. |
| 5,067,345 | A * | 11/1991 | Mougne ............ G01N 33/2823 |
| | | | 73/61.44 |
| 5,275,957 | A | 1/1994 | Blades et al. |
| 6,028,433 | A * | 2/2000 | Cheiky-Zelina ... G01N 33/2888 |
| | | | 324/663 |
| 2009/0315574 | A1 | 12/2009 | Akiyama et al. |
| 2010/0188111 | A1 | 7/2010 | Fougere |
| 2013/0293246 | A1 * | 11/2013 | Pollack ............. B01L 3/502784 |
| | | | 324/671 |

FOREIGN PATENT DOCUMENTS

| | | |
|---|---|---|
| JP | 2002-195867 A | 7/2002 |
| JP | 2009-2693 A | 1/2009 |
| KR | 1020160088779 A | 7/2016 |

OTHER PUBLICATIONS

International Search Report and Written Opinion in PCT/JP2018/007800, dated May 22, 2018. 10pp.

* cited by examiner

FLUID PROPERTY DETECTION DEVICE

RELATED APPLICATIONS

The present application is National Phase of International Application Number PCT/JP2018/007800, filed Mar. 1, 2018, and claims priority based on Japanese Patent Application No. 2017-049789, filed Mar. 15, 2017.

TECHNICAL FIELD

The present invention relates to fluid property detecting device configured to detect properties of a fluid.

BACKGROUND ART

JP2009-2693A discloses a fluid property detecting device including a detection portion arranged by facing a fluid and configured to detect electric characteristics of the fluid and a calculation portion configured to calculate a property value of the fluid such as conductivity on the bases of a detected detection value. Since the electric characteristics of the fluid detected by the detection portion of such fluid property detecting device have extremely small values, in order to make the detection value detected by the detection portion usable in the calculation portion, a circuit element such as an op amplifier or the like configured to apply amplification processing to the detection value is provided in the detection portion.

SUMMARY OF INVENTION

However, an error specific to the circuit element is superposed on a value outputted from the circuit element such as an op amplifier or the like in general. Since the value inputted into the circuit element in the fluid property detecting device is extremely small, the value outputted from the detection portion to the calculation portion through the circuit element includes errors at a relatively high rate. If a relatively high rate of errors is included in the values used for the calculation, even if the property value of the fluid is changed, the change does not appear easily in a value calculated in the calculation portion and as a result, it becomes difficult to determine the change in the properties of the fluid on the basis of the values outputted from the fluid property detecting device.

Moreover, since the errors of the circuit elements are different depending on the individual circuit elements, even if the properties of the same fluid are to be detected, when the fluid property detecting device is different, a magnitude of the detection value becomes different. Therefore, it becomes difficult to identify a type of the fluid of the like on the basis of the value detected by the fluid property detecting device.

The present invention has an object to improve detection accuracy of the fluid property detecting device.

According to one aspect of the present invention, a fluid property detecting device configured to detect properties of a detection target fluid, includes: a detection portion arranged by facing the detection target fluid and configured to detect electric characteristics of the detection target fluid; a calculation portion configured to calculate a property value of the detection target fluid on the basis of a detection value detected by the detection portion; and a storage portion configured to store the property value calculated by the calculation portion. The storage portion stores, in advance, as a reference detection value, a value of the electric characteristic of a reference fluid detected by the detection portion, the reference fluid having conductivity smaller than conductivity of the detection target fluid; and the calculation portion calculates the property value of the detection target fluid on the basis of a value obtained by subtracting the reference detection value from the detection value of the detection target fluid outputted from the detection portion.

DESCRIPTION OF EMBODIMENTS

A fluid property detecting device according to an embodiment of the present invention will be described below by referring to the attached drawings.

For example, the fluid property detecting device is attached directly to a fluid pressure device such as a hydraulic cylinder driven by a working oil as a working fluid or attached to a pipeline connected to the hydraulic cylinder or the like and detects properties of the working oil. A detection target of the fluid property detecting device is not limited to the working oil but may be various liquids and gases such as a lubricant oil, a cutting oil, a fuel, a solvent, a chemical and the like. In the following, a case where the fluid property detecting device is an oil property detecting device 100 which detects properties of the working oil as a detection target fluid will be described.

Figure 1:
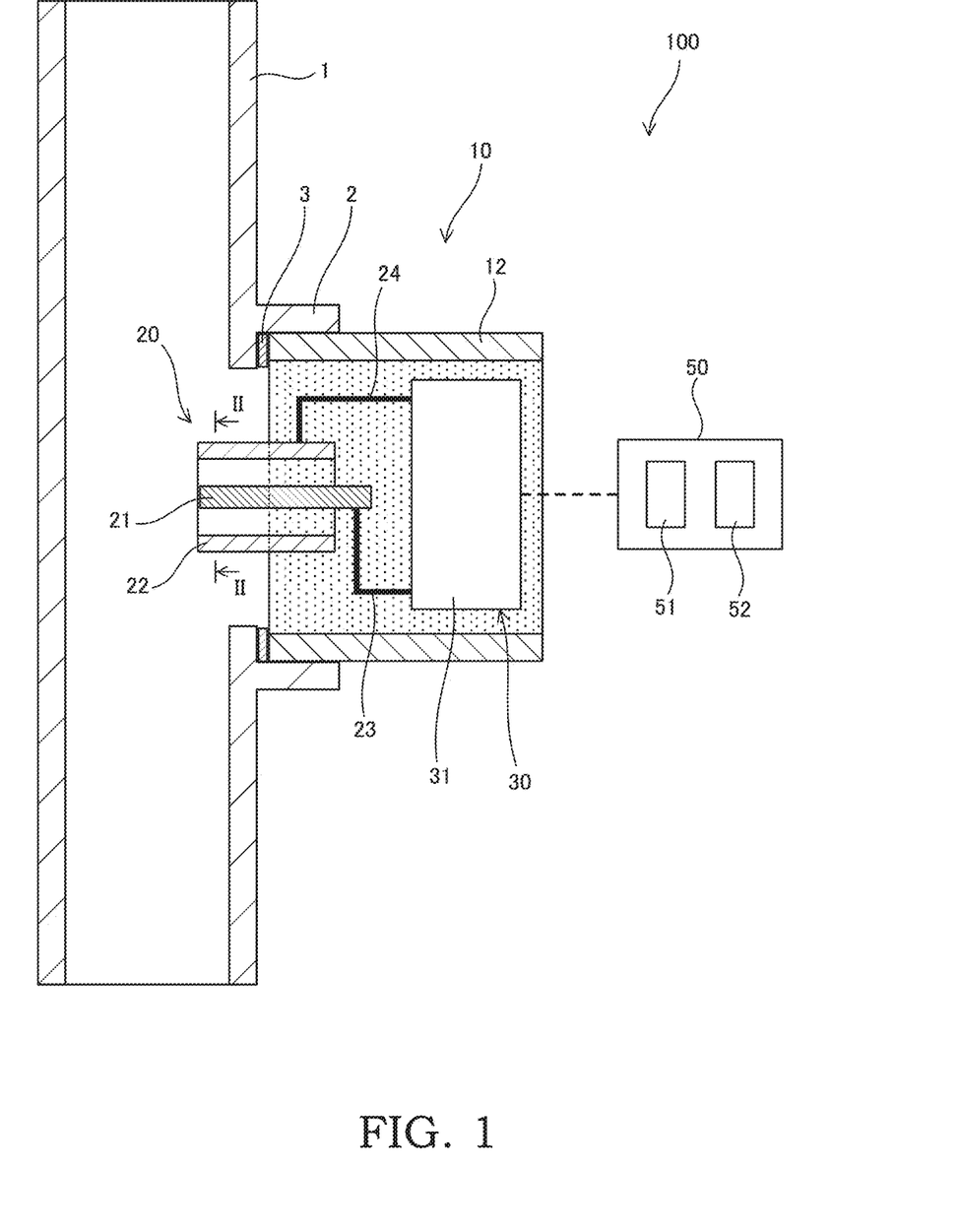
FIG. 1 is a schematic diagram illustrating configuration of a fluid property detecting device according to an embodiment of the present invention.

The oil property detecting device 100 has a detection portion 10 attached to a pipeline 1 through which the working oil flows configured to detect electric characteristics of the working oil and a control portion 50 which instructs detection of the electric characteristics of the working oil to the detection portion 10 and into which a detection value detected by the detection portion 10 is inputted.

The detection portion 10 has a casing 12 connected to a holder portion 2 formed on the pipeline 1, a pair of electrodes 20 exposed to the working oil, and a detection circuit 30 to which the pair of electrodes 20 is electrically connected. The casing 12 is a cylindrical member, and the pair of electrodes 20 and the detection circuit 30 are accommodated in the casing 12.

A gasket 3 is provided between the casing 12 and the holder portion 2, and leakage of the working oil to an outside through gap between the holder portion 2 and the casing 12 is prevented by the gasket 3. The holder portion 2 and the casing 12 are screwed with each other by a screw portion, not shown. A connecting method between the holder portion 2 and the casing 12 is not limited to screwing but may be fitting or may be connection using a fastening member such as a bolt.

The pair of electrodes 20 has a rod-shaped first electrode 21 formed having a columnar shape and a second electrode 22 arranged by facing the first electrode 21 at a predetermined interval. The pair of electrodes 20 is fixed to the casing 12 through an insulating member, not shown, by a fastening member such as a screw, not shown, in a state distal end portions of the first electrode 21 and the second electrode 22 protrude from the casing 12.

Figure 2:
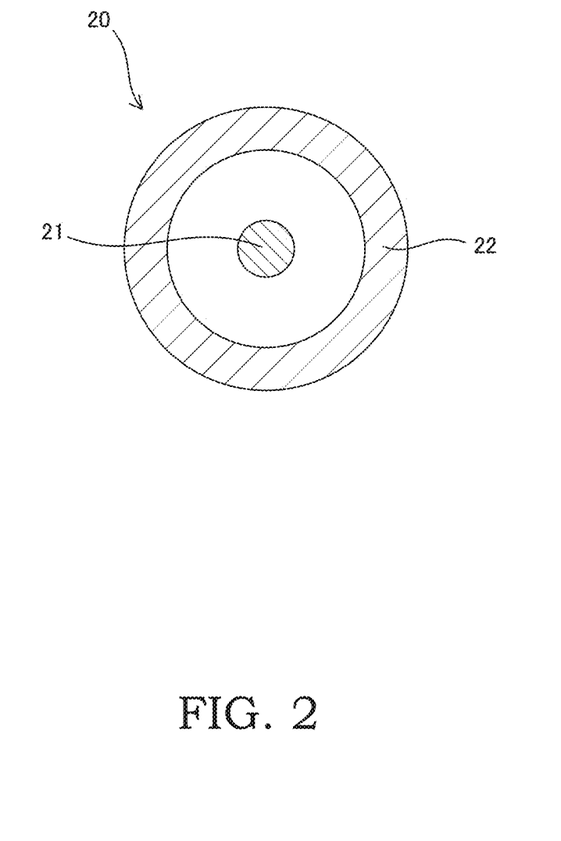
FIG. 2 is a sectional view illustrating a section along a II-II line in FIG. 1 in an enlarged manner.

The second electrode 22 is a cylindrical member as illustrated in FIG. 2 and is arranged on the same axis as the first electrode 21 so as to cover an outer periphery of the first electrode 21. A gap into which the working oil can enter is formed between the first electrode 21 and the second electrode 22 as described above. In the oil property detecting device 100, the property of the working oil interposed in the gap between the first electrode 21 and the second electrode 22 is detected. The first electrode 21 and the second electrode 22 are connected to the detection circuit 30 through wiring 23 and 24, respectively.

The detection circuit 30 is an electronic circuit on which a plurality of circuit elements, not shown, is provided on a substrate 31 and detects a voltage value applied between the pair of electrodes 20 and a voltage value correlated to a current value flowing between the pair of electrodes 20. The voltage value detected by the detection circuit 30 is outputted as the electric characteristic of the working oil to the control portion 50. The detection circuit 30 is fixed to the casing 12 by fastening the substrate 31 to the casing 12 by the fastening member such as a screw, not shown. The detection circuit 30 may be fixed to the casing 12 by insert molding together with the pair of electrodes 20.

Subsequently, specific configuration of the detection circuit 30 will be described by referring to FIG. 3.

The detection circuit 30 has a DC power supply 32 configured to output a predetermined voltage, a first switch 33 configured to apply a voltage of the DC power supply 32 to the first electrode 21, a second switch 34 configured to apply a voltage of the DC power supply 32 to the second electrode 22, a first current detection resistor 35 provided between the second switch 34 and the second electrode 22, a second current detection resistor 36 provided between the first switch 33 and the first electrode 21, a first resistor 37 having one end connected between the second switch 34 and first current detection resistor 35 and the other end grounded, and a second resistor 38 having one end connected between the first switch 33 and the second current detection resistor 36 and the other end grounded.

Switching of each of the first switch 33 and the second switch 34 is controlled by the control portion 50. When either one of the first switch 33 and the second switch 34 is connected, the other is open and controlled so that the both are not connected at the same time. It may be so configured that one three-position switch having a neutral position is provided instead of the two switches 33 and 34, and a connection state between the DC power supply 32 and the two electrodes 21 and 22 is switched by this switch.

The first current detection resistor 35 and the second current detection resistor 36 are highly accurate resistors having large resistance values provided in order to measure a micro current flowing through the circuit and have the same resistance values, respectively. The first resistor 37 and the second resistor 38 are resistors having the same resistance values, respectively.

The detection circuit 30 further has a first op amplifier 46 and a second op amplifier 47 as amplifier elements configured to apply amplification processing to a voltage at a measurement point on the circuit and an A/D converter 48 into which the voltage at the measurement point on the circuit is inputted.

Figure 3:
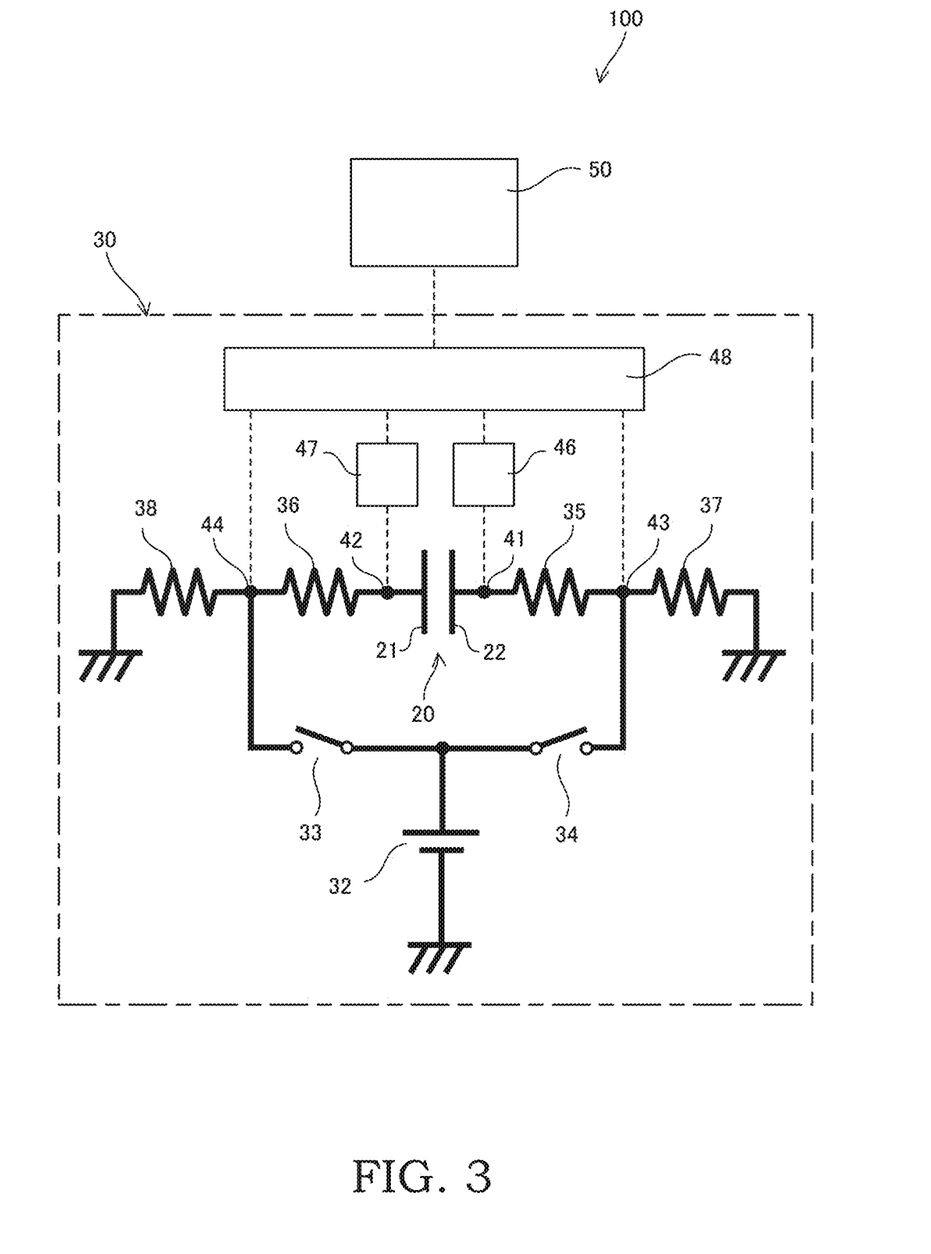
FIG. 3 is a schematic diagram illustrating configuration of a detection circuit of the fluid property detecting device.

A voltage value at a first measurement point 41 between the second electrode 22 and the first current detection resistor 35 is inputted into the A/D converter 48 through the first op amplifier 46, and a voltage value at a second measurement point 42 between the first electrode 21 and the second current detection resistor 36 is inputted into the A/D converter 48 through the second op amplifier 47 as illustrated in FIG. 3. Moreover, a voltage value at a third measurement point 43 between the second switch 34 and the first current detection resistor 35 and a voltage value at a fourth measurement point 44 between the first switch 33 and the second current detection resistor 36 are inputted into the A/D converter 48, respectively.

The voltage value inputted into the A/D converter 48 as described above is converted from an analog signal to a digital signal in the A/D converter 48 and then, outputted to the control portion 50.

The control portion 50 is a microcomputer and has a calculation portion 51 configured to calculate conductivity which is a property value of the working oil on the basis of the voltage value which is an electric characteristic of the working oil detected by the detection portion 10, a storage portion 52 capable of storing the conductivity calculated in the calculation portion 51 and the voltage value detected by the detection portion 10, an auxiliary storage portion such as a ROM and a RAM, not shown, which store a program used in the calculation portion 51 and the like, and an input/output interface (I/O interface), not shown. The calculation portion 51 is a so-called central processing unit (CPU), and the storage portion 52 is a non-volatile memory such as a rewritable EEPROM. The control portion 50 is connected to the detection circuit 30 through a wiring and is arranged outside of the casing 12. The control portion 50 may be arranged inside the casing 12 in a state provided on the substrate 31 together with the detection circuit 30, and in this case, the control portion 50 is fixed to the casing 12 by fastening the substrate 31 to the casing 12 by a fastening member such as a screw, not shown. Moreover, the control portion 50 may be fixed to the casing 12 by insert molding together with the pair of electrodes 20 and the detection circuit 30.

Subsequently, property detection of the working oil by the oil property detecting device 100 with the aforementioned configuration will be described.

In the oil property detecting device 100, first, detection of the electric characteristics of a reference fluid having conductivity smaller than that of the working oil is made as a preparation stage before detection of the properties of the working oil which is a detection target fluid.

A fluid having conductivity of one thousandth or less of that of the detection target fluid, that is, a fluid having resistance of 1000 times or more of that of the working oil is used as the reference fluid. Fluids having extremely small conductivity include super pure water and the like, but air is preferably used by considering workability and costs. The electric characteristics of the air can be easily detected by exposing the pair of electrodes 20 in the air.

Specifically, the first switch 33 is connected in a state where the pair of electrodes 20 is exposed in the air. When the first switch 33 is connected, a voltage of the DC power supply 32 is applied to the first electrode 21, and the second electrode 22 is brought into a grounded state through the resistors 35 and 37. Since the air existing between the pair of electrodes 20 has slight conductivity, a slight electric current flows between the first electrode 21 and the second electrode 22, and this electric current flows also to the first current detection resistor 35.

In this state, a voltage value at the first measurement point 41 is inputted into the A/D converter 48 through the first op amplifier 46. As described above, the voltage value amplified by the first op amplifier 46 is inputted into the control portion 50 through the A/D converter 48 and stored in the storage portion 52 as a first reference detection value.

Subsequently, the first switch 33 is opened, and the second switch 34 is connected. When the second switch 34 is connected, the voltage of the DC power supply 32 is applied to the second electrode 22, and the first electrode 21 is brought into the grounded state through the resistors 36 and 38. In this case, too, a slight electric current flows between the first electrode 21 and the second electrode 22, and this electric current flows also to the second current detection resistor 36.

In this state, the voltage value at the second measurement point 42 is inputted into the A/D converter 48 through the second op amplifier 47. As described above, the voltage value amplified by the second op amplifier 47 is inputted into the control portion 50 through the A/D converter 48 and stored in the storage portion 52 as a second reference detection value.

When the preparation stage is completed by storing the first reference detection value and the second reference detection value in the storage portion 52 as describe above, the properties of the working oil which is the detection target fluid can be detected by the oil property detecting device 100.

In order to detect the properties of the working oil, first, the first switch 33 is connected in a state where the pair of electrodes 20 is immersed in the working oil. When the first switch 33 is connected, the voltage of the DC power supply 32 is applied to the first electrode 21, and the second electrode 22 is brought into the grounded state through the resistors 35 and 37. Since the working oil existing between the pair of electrodes 20 has slight conductivity, a slight electric current flows between the first electrode 21 and the second electrode 22, this electric current flows also to the first current detection resistor 35.

In this state, a first voltage value at the first measurement point 41 is inputted into the A/D converter 48 through the first op amplifier 46. This first voltage value is converted to a digital signal in the A/D converter 48 and outputted to the calculation portion 51 of the control portion 50 as a first detection value. Moreover, in this state, the voltage value at the third measurement point 43 is inputted into the A/D converter 48, and this voltage value is converted to a digital signal in the AD converter 48 and outputted to the calculation portion 51 of the control portion 50 together with the first voltage value.

In the calculation portion 51, first conductivity as a first property value of the working oil is calculated on the basis of the inputted voltage value.

In the calculation portion 51, in calculating a current value flowing between the pair of electrodes 20, the first reference voltage value stored in the storage portion 52 as the first reference detection value is subtracted from the first voltage value as the first detection value at the first measurement point 41 amplified by the first op amplifier 46.

Here, an error specific to the circuit element is superposed on the value outputted from the circuit element such as the op amplifier 46, 47 and the A/D converter 48 provided in the detection circuit 30. Particularly, since the voltage value inputted into the first op amplifier 46 in the oil property detecting device 100 is extremely small, a relatively high rate of errors is included when it is amplified by the first op amplifier 46. If the relatively high rate of errors is included in the value used for the calculation as above, it becomes difficult to calculate accurate conductivity of the working oil.

Thus, in this embodiment, in order to remove the error caused by the circuit element from the value used for the calculation in the calculation portion 51, the first reference voltage value stored in the storage portion 52 as the first reference detection value which is the voltage value detected at the first measurement point 41 when the air is a detection target is subtracted from the first voltage value at the first measurement point 41 amplified by the first op amplifier 46 as described above. Reasons for that will be described below.

Figure 4:
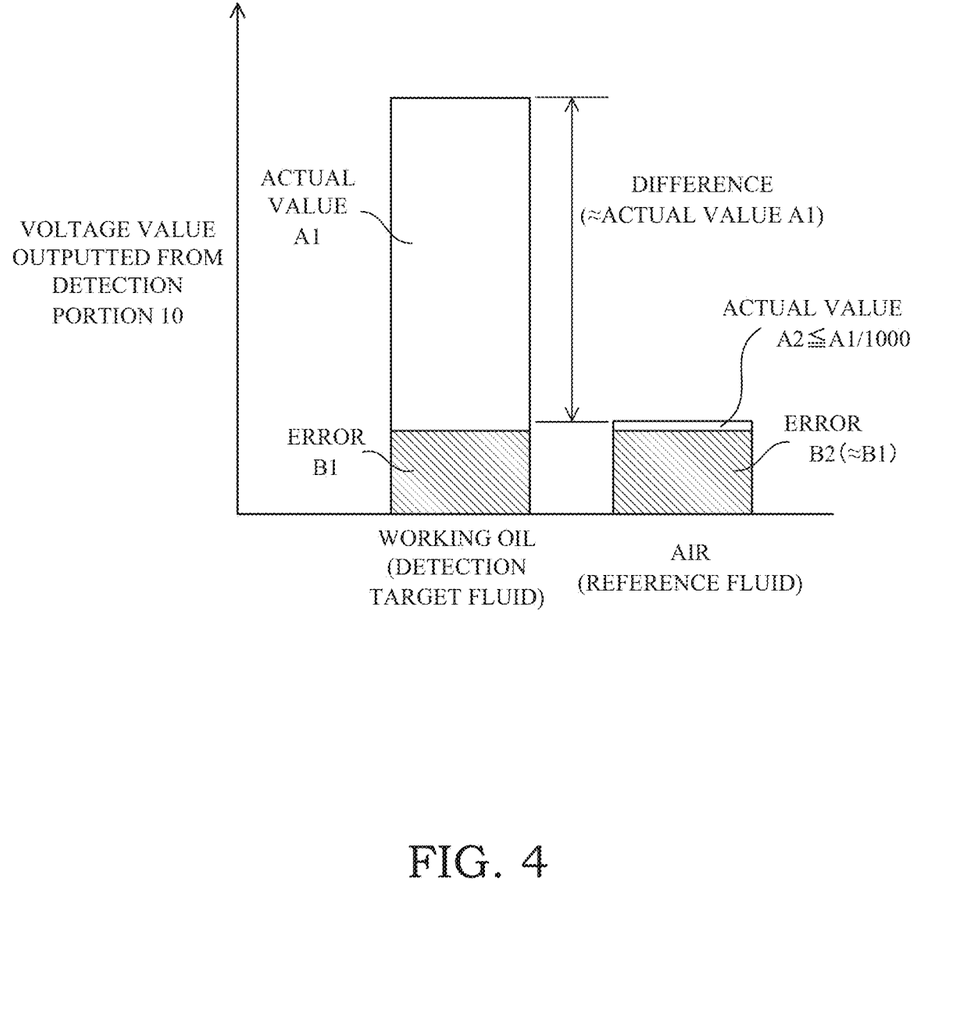
FIG. 4 is an image diagram of a voltage value outputted from a detection portion of the fluid property detecting device.

As illustrated as an image diagram in FIG. 4, a magnitude of the first voltage value outputted from the detection portion 10 when the working oil is a detection target and the magnitude of the first reference voltage value outputted from the detection portion 10 when the air is a detection target are largely different since the conductivity of the air is one thousandth or less of the conductivity of the working oil. On the other hand, both include the error caused by the circuit element such as the first op amplifier 46 and the A/D converter 48 to the same degree.

Specifically, the first voltage value when the working oil is the detection target includes an actual value A1 and an error B1, and the first reference voltage value when the air is the detection target includes an actual value A2 and an error B2. Since these voltage values are outputted along the same path, the errors B1 and B2 caused by the circuit element have values of approximately the same degree. On the other hand, the actual value A2 when the air is the detection target is one thousandth or less of the actual value A1 when the working oil is the detection target. Therefore, a difference obtained by subtracting the first reference voltage value when the air is the detection target from the first voltage value when the working oil is the detection target is a value extremely close to the actual value A1 when the working oil is the detection target.

As described above, the voltage value close to the actual value is calculated by subtracting the first reference voltage value stored in the storage portion 52 as the first reference detection value from the first voltage value at the first measurement point 41 amplified by the first op amplifier 46, and the voltage value applied to the first current detection resistor 35 is calculated on the basis of the calculated voltage value and the voltage value at the third measurement point 43.

Then, the current value flowing between the pair of electrodes 20, that is, the current value flowing through the first current detection resistor 35 is calculated from the known resistance value of the first current detection resistor 35 and the calculated voltage value applied to the first current detection resistor 35 on the basis of Ohm's law.

A resistance value of the working oil existing between the pair of electrodes 20 is calculated from the current value flowing between the pair of electrodes 20 calculated as above and the known voltage value applied to the pair of electrodes 20. Then, the first conductivity of the working oil is derived from a known relational expression on the basis of the calculated resistance value and the shapes of the pair of electrodes 20. The first conductivity calculated by the calculation portion 51 is stored in the storage portion 52 as the first property value. The voltage value applied between the pair of electrodes 20 may be calculated from the known voltage value of the DC power supply 32 and the voltage value at the third measurement point 43.

Subsequently, the first switch 33 is opened, and the second switch 34 is connected. When the second switch 34 is connected, the voltage of the DC power supply 32 is applied to the second electrode 22, and the first electrode 21 is brought to the grounded state through the resistors 36 and 38. In this case, too, a slight electric current flows between the first electrode 21 and the second electrode 22, and this electric current flows also to the second current detection resistor 36.

In this state, the second voltage value at the second measurement point 42 is inputted into the A/D converter 48 through the second op amplifier 47. This second voltage value is converted to a digital signal in the A/D converter 48 and outputted to the calculation portion 51 of the control portion 50 as the second voltage value. Moreover, in this state, the voltage value at the fourth measurement point 44 is inputted into the A/D converter 48, converted to a digital signal in the A/D converter 48, and is outputted to the calculation portion 51 of the control portion 50 together with the second voltage value.

In the calculation portion 51, second conductivity as a second property value of the working oil is calculated on the basis of the inputted voltage value. The second conductivity calculated in the calculation portion 51 is stored in the storage portion 52 as the second property value. Since the calculation of the second conductivity is made through a process similar to the calculation of the aforementioned first conductivity, detailed description will be omitted.

Each of the property values stored in the storage portion 52 is compared with the property values calculated in the past in a comparison portion, not shown, for example, and used for deterioration determination of the working oil. Each of the property values stored in the storage portion 52 may be transmitted to a server for analyzing the working oil or the like disposed at a remote site through a communication portion, not shown.

As described above, in the oil property detecting device 100, the property values of the working oil are calculated by using the values from which influences of errors caused by the circuit elements 46, 47, and 48 are removed. Thus, the property values of the working oil can be calculated with accuracy as compared with a case where the property values of the working oil are calculated by using the detection values outputted from the detection portion 10 through the circuit elements 46, 47, and 48 as they are.

Moreover, in the oil property detecting device 100, the electric characteristics of the working oil are detected separately between a case where the voltage of the DC power supply 32 is applied to the first electrode 21 and a case where the voltage of the DC power supply 32 is applied to the second electrode 22, and the property values calculated on the basis of the respective detection values are stored separately. The reason why the property values are calculated separately depending on the state where the DC power supply 32 is applied as above is that the shapes of the first electrode 21 and the second electrode 22 are different. This point will be described below.

When the first electrode 21 has a rod shape and the second electrode 22 is a cylindrical member as in this embodiment, rigidity of the pair of electrodes 20 becomes higher than a case where the first electrode and the second electrode are flat plates having the same shape faced with each other, and durability of the oil property detecting device 100 can be improved. Thus, even if the oil property detecting device 100 is mounted on a portion where flow velocity of the working oil is fast, for example, the property value of the working oil can be detected with accuracy for a long period of time.

On the other hand, if the shapes of the first electrode 21 and the second electrode 22 are made different, it is likely that a current channel from the first electrode 21 to the second electrode 22 and a current channel from the second electrode 22 to the first electrode 21 are different, and even if the same voltage is applied to each of the electrodes, there is a concern that the current values flowing between the electrodes are not the same. That is, there is a concern that a difference is generated between the first property value calculated when the voltage is applied to the first electrode 21 and the second property value calculated when the voltage is applied to the second electrode 22.

Thus, in order to detect a more accurate property value, the first property value and the second property value are calculated separately. In order to detect a more accurate property value, it is preferable that the electric characteristics of the working oil are detected a plurality of times, and each of the property values is calculated on the basis of an average value thereof. Moreover, the average value of the first property value and the second property value may be stored in the storage portion 52 as the property value of the working oil.

According to the embodiment described above, effects illustrated below are exerted.

In the oil property detecting device 100 with the aforementioned configuration, the property value of the working oil is calculated on the basis of the value obtained by subtracting the reference detection value indicating the electric characteristic of the air from the detection value indicating the electric characteristic of the working oil outputted from the detection portion 10 through the circuit elements 46, 47, and 48. The detection value of the working oil and the reference detection value of the air having conductivity smaller than that of the working oil have largely different absolute values, but the both include the errors caused by the circuit elements 46, 47, and 48 to the same degree. That is, by subtracting the reference detection value of the air detected by the detection portion 10 from the detection value of the working oil detected by the detection portion 10, the detection value of the working oil from which the influence of the error was removed can be obtained. In the calculation portion 51 as described above, the property value of the working oil is calculated on the basis of the detection value from which the influence of the error generated when the electric characteristics were detected was removed. As a result, detection accuracy of the property value of the working oil by the oil property detecting device 100 can be improved.

In the oil property detecting device 100 according to the aforementioned embodiment, conductivity is calculated as the property value of the working oil. The property value is not limited to that and may be any value as long as it is calculated on the basis of a value outputted through the circuit element and may be a capacitance value, viscosity or density.

Moreover, in the oil property detecting device 100 according to the aforementioned embodiment, when the property value of the working oil is to be detected, the voltage of the DC power supply 32 is applied alternately to the first electrode 21 and the second electrode 22. Instead of this, it may be so configured that, when the property value of the working oil is to be detected, a voltage of an AC power supply is applied alternately to the first electrode 21 and the second electrode 22. In this case, the resistance value between the pair of electrodes 20 can be calculated by using a well-known calculation equation by measuring impedance.

Moreover, in the oil property detecting device 100 according to the aforementioned embodiment, the air is used as the reference fluid. The reference fluid is not limited to the air but may be any fluid as long as it has conductivity smaller than that of the detection target fluid. The smaller the conductivity of the reference fluid is than the detection target fluid, the more accurately the conductivity of the detection target fluid can be calculated.

The configuration, the action, and the effects of the embodiment of the present invention configured as above will be described altogether.

The oil property detecting device 100 includes the detection portion 10 arranged by facing the working oil and configured to detect the electric characteristics of the working oil, the calculation portion 51 configured to calculate the property value of the working oil on the basis of the detection value detected by the detection portion 10, and the storage portion 52 configured to store the property value calculated by the calculation portion 51, and the storage portion 52 stores, in advance, as the reference detection value, the detection value of the electric characteristic of the air having conductivity smaller than that of the working oil detected by the detection portion 10, and the calculation portion 51 calculates the property value of the working oil on the basis of the value obtained by subtracting the reference detection value from the detection value of the working oil outputted from the detection portion 10.

In this configuration, the property value of the working oil is calculated on the basis of the value obtained by subtracting the reference detection value indicating the electric characteristic of the air from the detection value indicating the electric characteristic of the working oil outputted from the detection portion 10 through the circuit elements 46, 47, and 48. The detection value of the working oil and the reference detection value of the air having conductivity smaller than that of the working oil have largely different absolute values but the both include the error caused by the circuit elements 46, 47, and 48 provided in the detection portion 10 to the same degree. That is, by subtracting the reference detection value of the air detected similarly by the detection portion 10 from the detection value of the working oil detected by the detection portion 10, the detection value of the working oil from which the influence of the error was removed can be obtained. As described above, in the calculation portion 51, the property value of the working oil is calculated on the basis of the detection value from which the influence of the error generated when the electric characteristic was detected was removed. As a result, detection accuracy of the property values of the working oil by the oil property detecting device 100 can be improved.

Moreover, the property value outputted from the oil property detecting device 100 include few errors caused by the circuit elements 46, 47, 48 and the like and thus, even if the properties of the working oil are slightly changed, a change occurs in the calculated property value. Therefore, a deterioration state of the working oil can be detected with accuracy. Moreover, the property values outputted from the oil property detecting device 100 include few errors caused by the circuit elements 46, 47, 48 and the like but are values close to actual values and thus, a type of the working oil can be specified on the basis of the property values.

Moreover, the detection portion 10 has the op amplifiers 46 and 47 configured to apply amplification processing to the detection value.

In this configuration, the detection value detected by the detection portion 10 is inputted into the op amplifiers 46 and 47 and is subjected to the amplification processing. A relatively large error is superposed particularly on a value outputted from the circuit element which executes amplification processing such as the op amplifiers 46 and 47. However, by subtracting the reference detection value of the air detected similarly by the detection portion 10 through the op amplifiers 46 and 47 from the detection value of the working oil detected by the detection portion 10 through the op amplifiers 46 and 47, the detection value of the working oil from which the influence of the error caused by the op amplifiers 46 and 47 was removed can be obtained. Thus, even if the op amplifiers 46 and 47 are used as above, too, the detection accuracy of the property values of the working oil by the oil property detecting device 100 can be improved.

Moreover, the detection portion 10 has the pair of electrodes 20 exposed to the working oil, the pair of electrodes 20 has the first electrode 21 and the second electrode 22 arranged by facing the first electrode 21 and having the shape different from that of the first electrode 21, and in a state where the pair of electrodes 20 are exposed to the working oil, the calculation portion 51 calculates the first property value of the working oil on the basis of the first detection value of the working oil detected by the detection portion 10 when the voltage is applied to the first electrode 21, and calculates the second property value of the working oil on the basis of the second detection value of the working oil detected by the detection portion 10 when the voltage is applied to the second electrode 22.

When the shapes of the first electrode 21 and the second electrode 22 are different, there is a concern that the current value flowing between the electrodes do not become the same even if the same voltage is applied to each of the electrodes. On the other hand, in this configuration, the detection of the electric characteristics of the working oil is made separately for the case where the voltage is applied to the first electrode 21 and the case where the voltage is applied to the second electrode 22 having the shape different from that of the first electrode 21, and the property value is calculated on the basis of the respective detection values. As described above, by calculating the property values separately for the case where the voltage is applied to the first electrode 21 and the case where the voltage is applied to the second electrode 22, the property values of the working oil can be detected more accurately.

Moreover, in the state where the pair of electrodes 20 is exposed to the air, the storage portion 52 stores the first reference detection value detected by the detection portion 10 when the voltage is applied to the first electrode 21 and the second reference detection value detected by the detection portion 10 when the voltage is applied to the second electrode 22 in advance, and in the state where the pair of electrodes 20 is exposed to the working oil, the calculation portion 51 calculates the first property value on the basis of the value obtained by subtracting the first reference detection value from the first detection value when the voltage is applied to the first electrode 21 and calculates the second property value on the basis of the value obtained by subtracting the second reference detection value from the second detection value when the voltage is applied to the second electrode 22.

In this configuration, the detection of the electric characteristics of the air is made in advance separately for the case where the voltage is applied to the first electrode 21 and the case where the voltage is applied to the second electrode 22 having the shape different from that of the first electrode 21. As described above, by calculating the property values on the basis of the detection value and the reference detection value separately for the case where the voltage is applied to the first electrode 21 and the case where the voltage is applied to the second voltage 22, the property values of the working oil can be detected more accurately.

Moreover, the first electrode 21 is a columnar rod-shaped member, and the second electrode 22 is a cylindrical member arranged on the same axis as the first electrode 21 so as to cover the outer periphery of the first electrode 21.

In this configuration, since the first electrode 21 is the columnar rod-shaped member and the second electrode 22 is the cylindrical member configuring the pair of electrodes 20, rigidity of the pair of electrodes 20 becomes higher than the case where the first electrode and the second electrode are flat plates having the same shape faced with each other. As a result, durability of the oil property detecting device 100 is improved, and the property values of the working oil can be detected with accuracy for a long period of time. Moreover, since the first electrode 21 is arranged on the inner side of the cylindrical second electrode 22, an electric field formed between the first electrode 21 and the second electrode 22 is formed on the inner side of the second electrode 22. Thus, even if there is a member made of metal around the second electrode 22, an influence of such member on the electric field formed between the first electrode 21 and the second electrode 22 is reduced, and as a result, generation of an error in the detection value by the influence of such member can be prevented.

Moreover, the reference fluid is air having conductivity of one thousandth or less of the conductivity of the working oil.

In this configuration, the air having the conductivity of one thousandth or less of the conductivity of the working oil is used as the reference fluid. The smaller the conductivity of the fluid used as the reference fluid is than the conductivity of the working oil, the closer the value obtained by subtracting the reference detection value from the detection value is to the actual detection value of the working oil. As a result, the detection accuracy of the property values of the working oil by the oil property detecting device 100 can be improved. Moreover, since the air is used as the reference fluid, detection of the reference detection value of the reference fluid can be made easily, and since there is no need to prepare the reference fluid in advance, a cost in detection of the property value of the working oil can be reduced.

Embodiments of the present invention were described above, but the above embodiments are merely examples of applications of the present invention, and the technical scope of the present invention is not limited to the specific constitutions of the above embodiments.

This application claims priority based on Japanese Patent Application No. 2017-049789 filed with the Japan Patent Office on Mar. 15, 2017, the entire contents of which are incorporated into this specification.

The invention claimed is:

1. A fluid property detecting device configured to detect properties of a detection target fluid, comprising:
   a detection portion arranged by facing the detection target fluid and configured to detect an electric characteristic of the detection target fluid;
   a calculation portion configured to calculate a property value of the detection target fluid on the basis of a detection value detected by the detection portion; and
   a storage portion configured to store the property value calculated by the calculation portion, wherein
   the storage portion is configured to store, in advance, a reference detection value of the electric characteristic of a reference fluid detected by the detection portion, the reference fluid having conductivity smaller than conductivity of the detection target fluid;
   the detection portion has a pair of electrodes exposed to the detection target fluid;
   the pair of electrodes has a first electrode and a second electrode arranged by facing the first electrode and having a shape different from that of the first electrode;
   the calculation portion is configured to calculate the property value of the detection target fluid by subtracting the reference detection value from the detection value of the detection target fluid outputted from the detection portion, and calculate, in a state where the pair of electrodes is exposed to the detection target fluid:
      a first property value of the detection target fluid on the basis of a first detection value of the detection target fluid, detected by the detection portion, when a voltage is applied to the first electrode; and
      a second property value of the detection target fluid on the basis of a second detection value of the detection target fluid, detected by the detection portion when the voltage is applied to the second electrode; and
   the calculation portion is configured to calculate the property value on the basis of the first property value and the second property value.

2. The fluid property detecting device according to claim 1, wherein
   the detection portion has an amplifier element configured to apply amplification processing to the detection value.

3. The fluid property detecting device according to claim 1, wherein
   the storage portion is configured to store, in advance, a first reference detection value detected by the detection portion when the voltage is applied to the first electrode and a second reference detection value detected by the detection portion when the voltage is applied to the second electrode in a state where the pair of electrodes is exposed to the reference fluid; and
   the calculation portion is configured to
      calculate the first property value by subtracting the first reference detection value from the first detection value, and
      calculate the second property value by subtracting the second reference detection value from the second detection value.

4. The fluid property detecting device according to claim 1, wherein
   the first electrode is a columnar rod-shaped member; and
   the second electrode is a cylindrical member arranged on the same axis as the first electrode and covering an outer periphery of the first electrode.

5. The fluid property detecting device according to claim 1, wherein
   the conductivity of the reference fluid is one thousandth or less of the conductivity of the detection target fluid.

* * * * *